US008257701B2

(12) United States Patent
Orbe Lopategui et al.

(10) Patent No.: US 8,257,701 B2
(45) Date of Patent: Sep. 4, 2012

(54) METHODS FOR ANTI-FIBRINOLYTIC TREATMENT USING MMP-10 NEUTRALIZING ANTIBODY

(75) Inventors: Josune Orbe Lopategui, Pamplona (ES); Jóse Antonio Rodríguez García, Pamplona (ES); José Antonio Páramo Fernández, Pamplona (ES); Rosario Serrano Vargas, Pamplona (ES)

(73) Assignee: Proyecto de Biomedicina Cima, S.L., Navarra (ES)

( * ) Notice: Subject to any disclaimer, the term of this patent is extended or adjusted under 35 U.S.C. 154(b) by 431 days.

(21) Appl. No.: 12/452,280

(22) PCT Filed: Jun. 26, 2008

(86) PCT No.: PCT/ES2008/000453
§ 371 (c)(1),
(2), (4) Date: Feb. 4, 2010

(87) PCT Pub. No.: WO2009/000957
PCT Pub. Date: Dec. 31, 2008

(65) Prior Publication Data
US 2010/0135986 A1    Jun. 3, 2010

(30) Foreign Application Priority Data
Jun. 26, 2007    (ES) .................................. P200701786

(51) Int. Cl.
*A61K 39/395*    (2006.01)
(52) U.S. Cl. ..................................................... 424/130.1
(58) Field of Classification Search ........................ None
See application file for complete search history.

(56) References Cited

U.S. PATENT DOCUMENTS
5,922,322 A    7/1999 Bini
2005/0281810 A1    12/2005 Bernstein et al.

FOREIGN PATENT DOCUMENTS
EP    1 060 747    12/2000

OTHER PUBLICATIONS

International Search Report issued Nov. 17, 2008 in International (PCT) Application No. PCT/ES2008/000453.
P. A. Lapchak et al., "Reducing Bleeding Complications after Thrombolytic Therapy for Stroke", CNS Drugs, vol. 15, No. 11, pp. 819-829, 2001.
P. A. Lapchak et al., "Metalloproteinase Inhibition Reduces Thrombolytic (Tissue Plasminogen Activator)-Induced Hemorrhage after Thromboembolic Stroke", Stroke, vol. 31, No. 12, pp. 3034-3040, Dec. 2000.
D. T. Mangano et al., "The Risk Associated with Aprotinin in Cardiac Surgery", The New England Journal of Medicine, vol. 354, pp. 353-365, Jan. 26, 2006.

M. T. de Boer et al., "Minimizing Blood Loss in Liver Transplantation: Progress through Research and Evolution of Techniques", Dig Surg vol. 22, pp. 265-275, 2005.
R. Al-Shahi Salman, "Hemostatic Drug Therapies for Acute Spontaneous Intracerebral hemorrhage", Cochrane Database Systematic Review, Issue 4, 2006, CD005951.
S. A. Mayer et al., "Recombinant Activated Factor VII for Acute Intracerebral Hemorrhage", The New England Journal of Medicine, vol. 352, No. 8, pp. 777-785, Feb. 24, 2005.
J. A. Paramo, "Coagulacion Intravascular Diseminada", Med. Clin. (Barc.), vol. 127, No. 20, pp. 785-789, 2006.
M. Franchini et al., "Dental Procedures in Adult Patients with Hereditary Bleeding Disorders: 10 Years Experience in Three Italian Hemophilia Centers", Haemopilia, vol. 11, pp. 504-509, 2005.
C. Demers et al., "Gynecological and Obstetric Management of Women with Inherited Bleeding Disorders", International Journal of Gynecology and Obstetrics, vol. 95, pp. 75-87, 2006.
M. Gabay, "Absorbable Hemostatic Agents", Am J. Health Syst. Pharm., vol. 64, pp. 1244-1253, Jul. 1, 2006.
J. T. Peterson, "The Importance of Estimating the Therapeutic Index in the Development of Matrix Metalloproteinase Inhibitors", Cardiovascular Research, vol. 69, pp. 677-687, 2006.
H. Nakamura et al., "Activation of the Precursor of Human Stromelysin 2 and its Interactions with Other Matrix Metalloproteinases", Eur. J. Biochem., vol. 253, pp. 67-75, 1998.
O. Rechardt et al., "Stromelysin-2 is Upregulated During Normal Wound Repair and is Inducted by Cytokines", J. Invest. Dermatol. vol. 115, No. 5, pp. 778-787, Nov. 2000.
De Quan Li et al., "Regulated Expression of Collagenases MMP-1, -8, and -13 and Stromelysins MMP-3, -10, and -11 by Human Corneal Epithelial Cells", Investigative Ophthalmology & Visual Science, vol. 44, No. 7, Jul. 2003.
I. Montero et al., "C-Reactive Protein Induces Matrix Metalloproteinase-1 and -10 in Human Endothelial Cells", Journal of the American college of Cardiology, vol. 47, No. 7, Apr. 4, 2006.
J. Orbe et al., "Independent Association of Matrix Metalloproteinase-10, Cardiovascular Risk Factors and Subclinical Atherosclerosis", Journal of Thrombosis and Haemostasis, vol. 5, pp. 91-97, 2007.
W. B. Saunders et al., "MMP-1 Activation by Serine Proteases and MMP-10 Induces Human Capillary Tubular Network Collapse and Regression in 3D collagen Matrices", Research Article, Journal of Cell Science, vol. 118, pp. 2325-2340, Feb. 23, 2005.
S. Chang et al., "Histone Deacetylase 7 Maintains Vascular Integrity by Repressing Matrix Metalloproteinase 10", Cell, vol. 126, pp. 321-334, Jul. 28, 2006.
M. Krampert et al., "Activities of the Matrix Metalloproteinase Stromelysin-2 (MMP-10) in Matrix Degradation and Keratinocyte Organization in Wounded Skin", Molecular Biology of the Cell, vol. 15, pp. 5242-5254, Dec. 2004.
G. Kohler et al., "Continuous Cultures of Fused Cells Secreting Antibody of Predefined Specificity", Nature, vol. 256, pp. 495-397, Aug. 7, 1975.
E. Harlow et al., "Using Antibodies, A Laboratory Manual", Publisher: Cold Spring Harbor Laboratory Press, Cold Spring Harbor, New York, 1998—ISBN 978-0879695439.

(Continued)

*Primary Examiner* — Sharon Wen
(74) *Attorney, Agent, or Firm* — Wenderoth, Lind & Ponack, L.L.P.

(57) ABSTRACT

The present invention concerns the use of a neutralizing antibody for matrix metalloproteinase-10 (MMP-10) in the preparation of a medicine useful for anti-fibrinolytic treatment, and for hemorrhages and hemorrhagic complications of various etiologies.

7 Claims, 6 Drawing Sheets

OTHER PUBLICATIONS

S. Dubel, "Handbook of Therapeutic Antibodies", Publisher: Wiley-VCH, 2007, vols. 1 and III—ISBN 978-3527314539.

"Antibodies: vol. 1: Production and Purification", de G. Subramanian Ed., Publisher: Springer, 1st ed, 2004—ISBN 978-0306482458.

"Antibodies: vol. 2: Novel Technologies and Therapeutic Use", de G. Subramanian Ed., Publisher: Springer, 1st, 2004—978-0306483158.

J. Sambrook et al., "Molecular Cloning: A Laboratory Manual", Publisher: Cold Spring Harbor Laboratory Press, 3th edition, 2001—ISBN 978-0879695774.

"Tecnologia Farmaceutica", de J.L. Vila Jato, 1997, vols. I and II, Ed. Sintesis, Madrid.

S. K. Niazi, "Handbook of Pharmaceutical Manufacturing Formulations", 2004, vols. I and VI, CRC Press, Boca Raton.

PA von dem Borne et al., "Feedback Activation of Factor XI by Thrombin in Plasma Results in Additional Formation of Thrombin that Protects Fibrin Clots from Fibrinolysis", Blood, vol. 86, pp. 3035-3042, 1995.

N. Edward, "Methods for Improving the Sensitivity and Specificity of the Fibrin Plate", J. Clin. Pathol., vol. 25, pp. 335-337, 1972.

METHODS FOR ANTI-FIBRINOLYTIC TREATMENT USING MMP-10 NEUTRALIZING ANTIBODY

This application is a U.S. national stage of International Application No. PCT/ES2008/000453 filed Jun. 26, 2008.

TECHNICAL FIELD OF THE INVENTION

This invention refers to the preparation of pharmaceutical compositions for anti-fibrinolytic treatment and haemorrhagic complications associated with hyper-fibrinolytic states or surgical procedures.

BACKGROUND TO THE INVENTION

The haemostatic system is responsible for maintaining circulatory fluidity and for preventing haemorrhage in response to vascular attack. Physiological haemostasis is controlled by mechanisms that promote coagulation and the formation of fibrin and by those favouring its degradation or fibrinolysis. Excessive activation of coagulation or a defect of fibrinolysis lead to the formation of clots that obstruct the blood vessels (intravascular thrombosis), causing ischemia and necrosis. However, a general situation of hyper-fibrinolysis encourages the beginning of haemorrhages.

Hyperfibrinolytic states caused by congenital abnormalities or acquired in the coagulation-fibrinolysis system cause predisposition to important haemorrhagic complications. Such states have been associated with thrombolytic treatment as well as with surgery in organs containing a high amount of plasminogen activators, such as the prostate glands, uterus and lung. Also, disseminated intravascular coagulation (DIC), secondary to many medical and/or surgical processes, constitutes the prototype of the hyper-fibrinolytic state associated with massive haemorrhage in various organs.

In diseases with underlying haemorrhagic physiopathology caused by abnormal coagulation or increase in fibrinolysis, and aside from following transfusions of haemoderivatives, the pharmacological measures for treatment are often anti-fibrinolytic, but the treatment fails in approximately 30% of the cases.

Anti-fibrinolytic treatments seek to inhibit degradation of fibrin. The most common ones used in clinical treatment are synthetic analogues of lysine, such as epsilon-aminocaproic acid (EACA) and tranexamic acid (AMCHA), which compete with plasminogen for lysine binding sites, and aprotinin, that is a derivative of bovine lung with a broad protease inhibition spectrum.

These compounds have been shown to be effective in various clinical medical and surgical situations, such as intracraneal haemorrhage, surgery with elevated risk of haemorrhage and complications derived from thrombolytic treatment.

At a surgical level, the anti-fibrinolytic agents, in addition to reducing post-operative haemorrhage, can be an alternative to blood transfusion and other haemoderivatives in heart, liver and orthopaedic surgery. However, the use of these preparations has not become generalised, in part because there are insufficient studies demonstrating their effectiveness and also because they may increase the risk of thrombolytic complications (Mangano DT et al. The risk associated with aprotinin in cardiac surgery. N Engl J Med 2006; 354: 353-365).

For example, in hepatic surgery, fundamentally liver transplant, the use of anti-fibrinolytics such as aprotinin and AMCHA achieves a reduction in haemorrhagic complications, but can be associated with thrombolytic problems (de Boer MT et al. Minimizing blood loss in liver transplants: progress through research and evolution of techniques. Dig Surg 2005; 22: 265-275).

In intracranial haemorrhage, the anti-fibrinolytics have also not been incorporated into the clinical practice guides (You H et al. Hemostatic drug therapies for acute intracerebral haemorrhage. Cochrane Database Syst Rev 2006; CD005951). In the particular case of brain haemorrhage, primary or secondary to thrombolytic treatment, the use of recombinant factor VIIa is the only treatment that seems to have any beneficial effect in terms of the reduction of mortality (29% of patients receiving placebo compared to 18% of patients receiving factor VIIa) and of reduction of neurological sequelae (Mayer S. A., Brun N. C. et al.; "Recombinant Activated Factor VII Intracerebral Hemorrhage Trial Investigators. Recombinant activated factor VII for acute intracerebral hemorrhage"; N Engl J Med. 2005; 352: 777-785].

Disseminated intravascular coagulation (DIC) is another clinical condition that involves massive haemorrhage in which the administration of current anti-fibrinolytics is contraindicated as it encourages generalised thrombosis (Paramo JA. Coagulación intravascular diseminada. Med clin (Barc) 2006; 127: 785-9).

Thrombolysis with tPA or urokinase type plasminogen activators is one of the treatments of choice in acute heart attack and ischemic stroke but its use is associated with a high incidence of major haemorrhaging in up to 14% of cases and of intracranial haemorrhage in up to 4% of cases. In addition to treatment with haemoderivatives, the EACA or AMCHA type anti-fibrinolytics are indicated when there is excessive haemorrhaging, although their use can encourage thrombotic recurrence.

Excessive haemorrhaging after teeth extraction is one of the more common complications in patients with congenital coagulopathies such as haemophilia A. In these situations, the local use of anti-fibrinolytic and anti-haemorrhagic agents (e.g. tranexamic acid, desmopressin and Factor VII) contribute to the persistence of the clot and prevention of haemorrhage (Franchini M et al. Dental procedures in adult patients with hereditary bleeding disorders: 10 years experience in three Italian Hemophila Centers. Haemophilia 2005; 11: 504-509).

Anti-fibrinolytics are also the first line of treatment in women with menorrhagia associated with congenital coagulopathies in combination with hormonal therapy (Demers C et al. Gynaecological and obstetric management of women with inherited bleeding disorders. J Obstet Gynaecol 2005; 27: 707-732).

The application of topical treatment with fibrin gels has been an advancement in preventing haemorrhaging related to surgical wounds but its clinical use has still not been established (Gabay M. Absorbable hemostatic agents. Am J Health Syst Pharm. 2006; 63: 1244-53).

The intravenous or topical application of inhibitors of MMPs can restore haemostasis more quickly, reducing local haemorrhagic complications or those associated with tPA (Lapchak P A, Araujo D M. Reducing bleeding complications after thrombolytic therapy for stroke: clinical potential of metalloproteinase inhibitors and spin trap agents. CNS Drugs. 2001; 15 :819-29), encouraging the persistence of the clot, the repair and the healing of surgical wounds. Although this is a promising strategic option, most clinical trials with inhibitors of MMPs have failed; either because of the low doses used (efficacy vs toxicity) or due to observed side effects (musculoskeletal syndrome). It would be necessary to find more selective inhibitors that only block the molecular mechanisms associated with a specific MMP thereby avoiding adverse effects (Peterson JT. The importance of estimating the therapeutic index in the development of matrix metalloproteinase inhibitors. Cardiovasc Res. 2006; 69: 677-687).

The purpose of the present invention is to provide alternative therapeutic compositions for anti-fibrinolytic treatment and for haemorrhagic complications that inhibit lysis of fibrin clots.

DETAILED DESCRIPTION OF THE INVENTION

Figure 1:
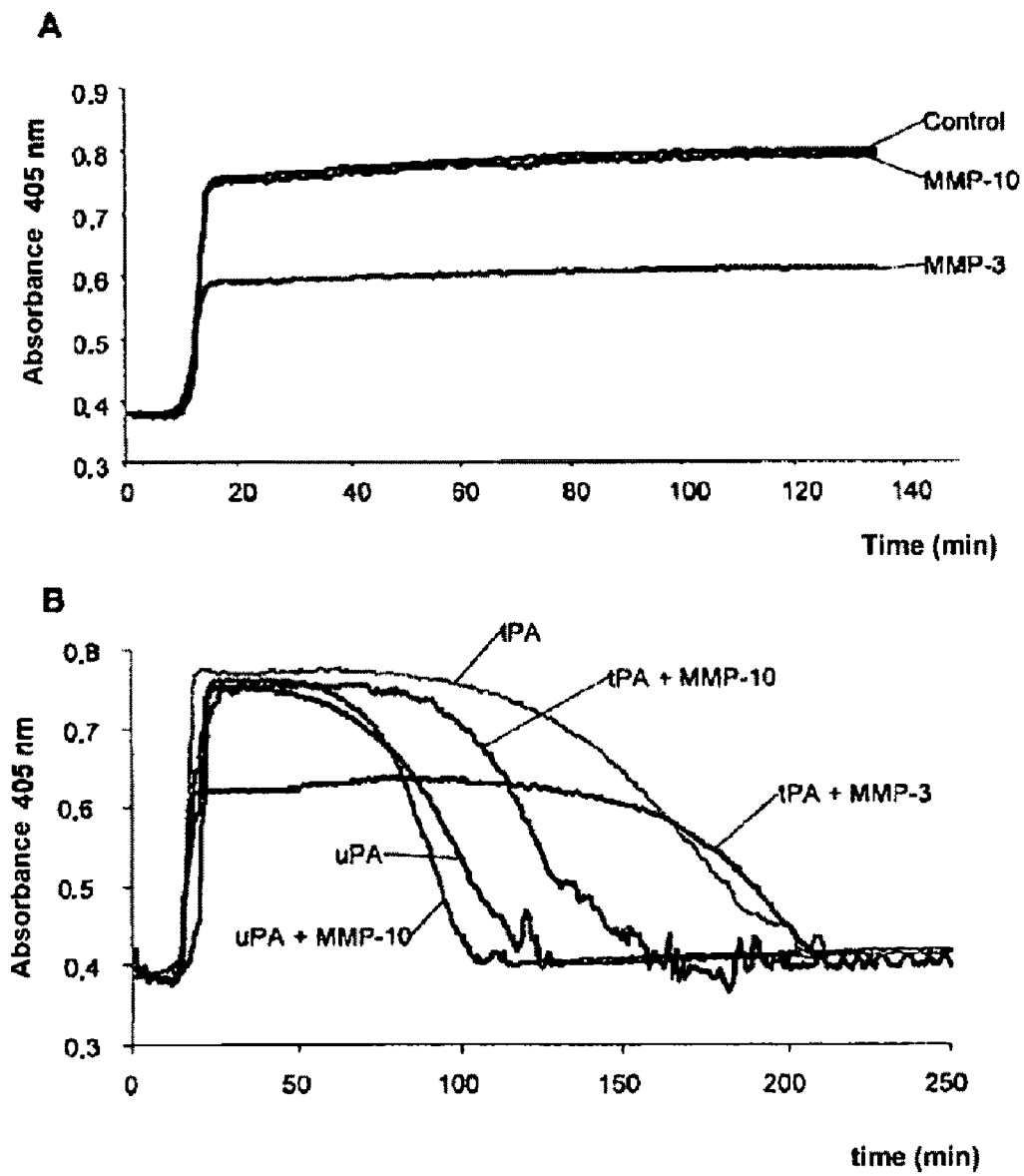
FIG. 1. Turbidimetric assay of recalcified plasma expressed as absorbance values at 405 nm against the duration of the experiment in minutes. A: The graph shows the differences in clot formation (maximum absorbance) of plasma alone (control) or in the presence of MMP-10 (200 nM) or MMP-3 (200 nM); B: The graph shows the formation and lysis of the recalcified plasma fibrin clot in the presence of plasminogen activators tPA (30 U/ml) and uPA (135 U/ml) alone, or combined with MMP-10 (200 nM) and also in the presence of an equivalent dose of MMP-3 (200 nM) combined with tPA (30 U/ml).

In a first aspect, the invention refers to the use of an antibody that neutralises matrix metalloproteinase-10 (MMP-10) in the preparation of a medicine for anti-fibrinolytic treatment.

MMP-10 (Enzyme code EC-Number 3.4.24.22) is also called matrix metallopeptidase, stromelysin-2 (STMY2), transin-2 or proteoglycanase-2. In humans, the gene coding for MMP-10 is located on chromosome 11 (11q22.3; HUGO Gene Nomenclature Committee HGNC-ID: 7156; UniProtKB/Swiss-Prot Accession Number: P09238).

This metalloproteinase is expressed by various cell types, such as endothelial cells, monocytes and fibroblasts. It is known that it can be activated by plasmin, calicrein, tryptase, elastase and cathepsin G and can degrade a wide range of extracellular matrix substrates, such as agrecane, elastin, fibronectin, gelatin, laminin, tenascin-C, vitronectin and collagen types II, III, IV, IX, X and XI. MMP-10 can also activate other matrix metalloproteinases, such as proMMP-1, -3, -7, -8 and -9 [Nakamura H et al.; Eur. J. Biochem., 1998; 253: 67-75].

It is also known that MMP-10 participates in various physiological processes, such as bone growth and wound healing. It is also over-expressed in corneas of patients with diabetic retinopathy and has been related to some types of carcinomas and also with lymphoid tumours. Various in vitro studies have demonstrated that the expression of MMP-10 in keratinocyte cultures can be induced by growth factors (epidermal growth factor of keratinocytes or TGF-beta) and by proinflammatory cytokines (TNF-alpha, IL-1beta) [Rechardt O et al.; J. Invest. Dermatol., 2000; 115: 778-787]; [Li de Q et al.; Invest. Opthalmol. Vis. Sci. 2003; 44: 2928-2936].

Likewise, in communications prior to this invention, it was described that MMP-10:

can be an inflammatory biomarker of vascular risk [Montero I et al.; J. Am. Col. Cardiol., 2006; 47: 1369-1378]; [Orbe J et al.; J. Thromb. Haemost.; 2007; 5: 91-97];

is induced in endothelial cells that form capillaries in 3D collagen matrices and participates in the regression of the formation of capillaries by the activation of MMP-1 [Saunders WB et al.; J. Cell Sci., 2005; 118:2325-2340]; and plays a fundamental role in the maintenance of intracellular unions that preserve vascular integrity in processes of remodelling and angiogenesis [Chang S et al.; Cell, 2006; 126: 321-334].

participates in healing of wounds, increasing the migration of keratinocytes and tissue reorganisation that occurs by the proteolytic degradation of matrix proteins [Krampert M, et al.; Mol Biol Cell, 2004; 5242-5254].

In the present invention, the effect of MMP-10 and MMP-3 on the formation and lysis of clots on human plasma were researched, as well as in other in vitro models of degradation of polymerised fibrin.

The inventors have been able to show that MMP-10 does not have direct thrombolytic activity and that it is not capable by itself of altering the formation of the clot nor degrading the fibrin. Surprisingly, they have also found that in the presence of thrombolysis activating agents, particularly plasminogen activators, MMP-10 encourages the dissolution of the fibrin clots and reduces the time of lysis. MMP-10 therefore acts as a facilitator or adjuvant of the thrombolytic action of other thrombolysis activators.

By contrast, a fibrinolytic matrix metalloproteinase such as MMP-3, with direct proteolytic activity on fibrin and fibrinogen, does not reduce clot lysis times, which activators of thrombolysis do by themselves.

Even more surprisingly, the inventors have found that the addition of antibodies specific against MMP-10 are capable of inhibiting the effect of MMP-10, leading to completely blocking the dissolution of the clot, even in the presence of fibrinolysis activators.

In consequence, a MMP-10 inhibiting agent, e.g. an antibody, could represent a significant advance in the control of haemorrhaging in medical and surgical areas, as well as being an alternative to blood transfusion in patients with excessive haemorrhaging caused by a fibrinolysis disorder, 1.—by its capacity to reduce and block the lysis of the fibrin clot even in the presence of plasminogen activators, 2.—by being a molecule that does not change the formation of the fibrin clot.

MMP-10, not being a protein that acts by a mechanism that is independent from the haemostatic system, does not present thrombolytic complications of conventional anti-fibrinolytics.

In addition, selective blocking of MMP-10 will not cause side effects associated with an non-selective inhibition of MMPs, such as the musculoskeletal syndrome, in which other MMPs such as MMP-9 and MMP-14 have been implicated.

MMP-10 Neutralising Antibody

Firstly, in the context of the invention, the term "antibody" includes polyclonal antibodies, monoclonal antibodies, recombinant antibodies, kimeric antibodies, humanised antibodies and fully human antibodies.

Polyclonal antibodies are originally heterogeneous mixtures of antibody molecules produced in the serum of animals that have been immunised with an antigen. They also include monospecific polyclonal antibodies obtained from heterogeneous mixtures, for example by chromatography in a column with peptides of a single epitope of the antigen of interest.

A monoclonal antibody is a homogeneous population of antibodies specific for a single epitope of the antigen. These monoclonal antibodies can be prepared by conventional techniques that have been already described, e.g. in Köhler and Milstein [Nature, 1975; 256: 495-397] or Harlow and Lane ["Using Antibodies. A Laboratory Manual" by E. Harlow and D. Lane, Publisher: Cold Spring Harbor Laboratory Press, Cold Spring Harbor, N.Y.; 1998 (ISBN 978-0879695439)].

A kimeric antibody is a monoclonal antibody constructed by cloning or recombination of antibodies from different animal species. In a typical but non-limiting configuration of the invention, the kimeric antibody includes a part of a monoclonal antibody, generally the variable region (Fv) that includes the sites for recognition and binding to the antigen and another part corresponding to a human antibody, generally the part including the constant region and the adjacent constant region.

A humanised antibody is a monoclonal antibody constructed by cloning and grafting the hyper-variable complementarity determining regions (CDR) of a murine monoclonal antibody into a human antibody, substituting its own hyper-variable CDR.

A totally human antibody is an antibody or antibodies that has been produced in transgenic animals with the human immune system or by immunisation in vitro of human immune cells (including both genetic immunisation and traditional, with and without adjuvants, and with pure or impure antigen; or by any method of exposure of the antigen to the immune system) or by native/synthetic libraries produced from human immune cells. These antibodies can be obtained and selected from transgenic animals (e.g. mice) into which genes of human immunoglobulins have been cloned and which are immunised with the target antigen. Equally, these antibodies can be obtained by selecting single-chain variable fragments (scFv) or by binding to human antigen (Fab) presented in phage libraries (phage display) and later cloning and grafting into a human antibody or by any other method of production and display) of the libraries generated by cloning the variable regions of both chains and later combination/mutation of these to generate antibody libraries.

Also, the antibody or antibodies of the invention can be of any of immunoglobulin class or subclass and particularly IgG, IgM, IgA, IgD and IgE.

In a particular embodiment, the antibodies are complete antibodies including all the functional regions that are typical of a natural immunoglobulin, particularly the regions for recognition and specific binding to the antigen.

Secondly, the term "antibody" also includes an antibody fragment, obtained from the protein or by recombinant technology, which expressed in prokaryotes, yeasts or eukaryotes, glycosylated or deglycosylated, and that can consist of the variable zones of antibodies linked to each other by a binding peptide (scFv) or the variable zone next to the CHI constant zone of the heavy chain (Fd) linked to the light chain by cysteins or by binding peptides and disulphide bridge (sc-Fab), or new variants, such as only heavy chains, or any modification that is made of these with the aim of making them more specific, less immunogenic (humanised) or more stable in biological fluids and that have the capacity of inhibiting MMP-10 by binding to its active centre or to any other domain of the protein that reduces its activity.

In the context of the invention, the terms "neutralising" or "antagonist" antibody of MMP-10 refers to an antibody, defined in the terms indicated above, that is capable of recognising and specifically binding to MMP-10 with an affinity in the nanomolar or picomolar range. Also, this antibody is capable of inhibiting or blocking, totally or partially, the activity of MMP-10. In particular, this antibody is capable of inhibiting or blocking the action of MMP-10 as facilitator of the dissolution of fibrin clots, reducing the lysis times (fibrinolytic-thrombolytic activity). In a particular embodiment, the neutralising antibody inhibits the adjuvant action that MMP-10 exercises over plasminogen activators (tPA, uPA, etc.).

Obtaining MMP-10 Neutralising Antibodies

The neutralising antibodies of the invention can be produced by the conventional methods already known for the production of antibodies. Without this representing any limitation, the methods used can include: immunisation techniques in animals, including transgenic animals for human immunoglobulin genes, production of monoclonal antibodies by hybridomas, production by antibody libraries, that can be native, synthetic or derived from organisms immunised against the antigen of interest and that can be selected by very different methods of presentation or display (phage display, ribosome display, etc.) and later by means of genetic engineering techniques may be redesigned and expressed in vectors designed for the production of recombinant antibodies of different sizes, compositions and structures. A review of the main methods for the production and purification of antibodies can be found in:

"Handbook of Therapeutic Antibodies", by S. Dübel, Publisher: Wiley-VCH, 2007, Vols: I to III (ISBN 978-3527314539);

"Antibodies: Volume 1: Production and Purification" by G. Subramanian Ed., Publisher: Springer, 1st Ed, 2004 (ISBN 978-0306482458);

"Antibodies: Volume 2: Novel Technologies and Therapeutic Use", by G. Subramanian Ed., Publisher: Springer, 1st Ed, 2004 (ISBN 978-0306483158);

"Molecular Cloning: a Laboratory manual", by J. Sambrook and D. W. Russel Eds., Publisher: Cold Spring Harbour Laboratory Press, 3rd edition, 2001 (ISBN 978-0879695774).

In a particular non-limiting embodiment of the invention, a procedure for obtaining and producing a neutralising monoclonal antibody of MMP-10 could comprise the following stages:

1.—Immunise mice with a solution of MMP-10 or an immunogenic fragment of MMP-10 or plasmid containing MMP-10 or derivatives.

2.—Select those animals with polyclonal response against the antigen by Western Blot, ELISA or immunocytochemistry.

3.—Perform the fusion of the animal spleens with myeloma cells (SP2/O-Ag14; P3×63-Ag8.6.5.3; P3-NS-I-Ag4-1; etc.) to generate hybrids between the different cell types: and select those hybrids of animal lymphocyte B and myeloma cells that produce antibody and are immortal in culture with HAT (hypoxanthine, aminopterin and thymidine) medium.

4.—Select the hybridomas that secrete antibodies of interest, in other words, antibodies that inhibit the activity of MMP-10. To do this, take samples of the supernatant of all the wells containing hybridomas to subject them to an immunoassay: perform ELISA assays with plates coated with ng or µg amounts of MMP-10; after incubation for 15 hours at 4° C. and blocking with a suitable protein, the supernatants of the cultures are added, the wells are washed and then a secondary mouse anti-immunoglobulin is added. After washing and developing with an enzymatic reaction, the wells in which colour is detected or which have an increase in absorbance can contain clones of hybridomas that secrete antibodies against MMP-10.

5.—Select those hybridomas capable of inhibiting the activity of MMP-10 by performing an assay with fluorogenic substrate. Use a microplate coated with various concentrations of an anti-MMP-10 antibody (R&D systems, Clon110343) and the flurogenic substrate of stromelysins (MCA-Arg-Pro-Lys-Pro-Val-Glu-Nval-Trp-Arg-Lys-[DNP]-NH2) (R&D systems; ES002, Abingdon, UK). The fluorescence (320 nm excitation and 405 nm emission is measured in a spectrofluorometer (SpectraMAX GeminiXS, Molecular Devices, CA, USA) for 2 h with reading every 5 min. In relation to a constant concentration of active MMP-10, those hybrids that reduce the activity of MMP-10 by at least 50% (IC50) at the lowest concentration and after preincubation with the protein for 30 min at 37° C. are selected.

The cells producing antibodies in the well from which the selected supernatant comes are grown and frozen in liquid nitrogen.

6.—Ensure that each culture of cells secreting an anti-MMP-10 antibody is monoclonal. Apply the techniques of cloning or limiting dilution and grow the isolated cells in new culture microplates starting from the original culture or stem cells that are positive in the first ELISA assay and activity assay. Once new colonies arising from one or more cells have acquired sufficient size, take new supernatants of these and subject them to a new ELISA and activity assay. Repeat the process until 100% of the supernatants analysed contain antibodies against the activity of MMP-10.

7.—Purify the antibodies from the supernatants by liquid chromatography (chromatography of immunoaffincity, affinity, cation exchange, hydroxyapatite, hydrophobic interaction, gel filtration, etc.) in a AKTA FPLC equipment, GE Healthcare Bio-Science.

8.—Lastly, analyse the purity, specificity, affinity and fibrinolytic activity of those that have been selected.

The antibody purity can be determined, for example, by polyacrylamide gel electrophoresis (SDS-PAGE) that is stained with Coomassie blue to demonstrate the presence of a single band.

The antibody specificity can be determined by Western blot against other metalloproteases (especially MMP-3 with which it shares the greatest homology) at ng to µg concentrations and developed by chemiluminescence.

The antibody affinity constant can be calculated from the dissociation constant (Kd), defined as the gradient obtained on representing the absorbance values of the ELISA coated with MMP-10 against increasing concentrations of antibody.

The neutralising capacity of the fibrinolytic activity of this antibody can be analysed by turbidimetric formation assay and lysis of fibrin clots and in polymerised fibrin assay, for example by the assays described in the examples 1 and 2.

Furthermore, the nucleic acid coding for the MMP-10 neutralising antibody can serve as an intermediate product for obtaining a kimeric or humanised antibody that is also a neutraliser of MMP-10.

Despite the above, the method for the production of the neutralising antibody of MMP-10 is not a critical aspect and therefore a person skilled in the art can easily produce the antibodies of the invention by means of any conventional method for the production of antibodies.

Therapeutic Indication for Anti-fibrinolytic Treatment

In general, the MMP-10 neutralising antibody (or the medicine containing it) is useful for anti-fibrinolytic treatment.

In a particular embodiment, the antibody of the invention is useful for the treatment, preventation or therapy, of haemorrhages or haemorrhagic complications.

In some cases, haemorrhagic complications to be treated can occur in patients with hyper-fibrinolytic states and coagulation defects that can be caused by congenital abnormalities (haemophilia A, von Willebrand disease, PAI-1 or alpha2-antiplasmin deficiency) or by acquired complications, e.g. derived from treatment with anti-coagulant agents or in patients with disseminated intravascular coagulation (DIC), some surgery or tumours of tissues or organs rich in fibrinolysis activators, or in situations of failure to clear plasminogen activators, such as severe liver disease or acute promyelocytic leukaemia associated with DIC.

Excessive haemorrhagic complications included among thesemenstrual haemorrhage (menorrhagia), gastrointestinal haemorrhage, urinary haemorrhage, tooth haemorrhage and particularly haemorrhage in patients with coagulation defects for some of the causes mentioned above (haemophilia A, von Willebrand disease, anti-coagulant treatment, DIC, etc.).

In other cases, haemorrhaging and haemorrhagic complications to be treated can occur in surgical procedures (surgery in general, including transplants and biopsies), particularly surgery on organs rich in plasminogen activators (prostate, lung, uterus) and in surgery on patients in hyper-fibrinolytic states or with the coagulation defects as already indicated. In these cases, the purpose is to reduce the haemorrhage derived from surgery by a treatment (prior, during and/or post surgery) with a medicine comprising a MMP-10 neutralising antibody.

Also, the topical use of anti-MMP-10 antibodies could be useful for restoring vascular communication after performing a vascular graft, including the inhibitor in a fibrin gel-type formulation to prevent the haemorrhaging related to the surgical wound.

In the context of the invention, the term "treatment" includes the administration of the medicine containing the MMP-10 neutralising antibody to prevent or reduce the beginning of symptoms, complications or biochemical indications of a hyper-fibrinolytic state, and most particularly to prevent the early existence of haemorrhagic events. The treatment can be a prophylactic treatment to prevent the manifestation of clinical or sub-clinical symptoms. It can also be a therapeutic treatment to suppress or alleviate the symptoms after they have appeared and can be an alternative to blood transfusion if that should be necessary.

Pharmaceutical Composition

According to the invention, neutralising antibodies are used in the preparation of a pharmaceutical composition as a medicine for anti-fibrinolytic treatment.

Said pharmaceutical composition comprises at least a MMP-10 neutralising antibody in a pharmaceutically acceptable vehicle.

The antibody or pharmaceutical composition of the invention is particularly useful for parenteral administration, for example for subcutaneous, intramuscular or intravenous administration.

In a specific but not limiting embodiment of the invention, the pharmaceutical composition contains a solution of neutralising antibody or antibodies against MMP-10 dissolved in an acceptable vehicle, e.g. an aqueous vehicle, such as water, buffered water, saline, glycine or other similar vehicle. These solutions are sterile and generally particulate free. The pharmaceutical composition can contain other additional ingredients, such as agents to adjust the pH, preservatives, etc.

In another embodiment, the pharmaceutical composition would be suitable for local administration, in the form of a gel or paste or even in the form of a drinkable ampoule of mouthwash in case of haemorrhages following dental extraction.

A review of the various compositions and pharmaceutical forms of medicine administration and of the excipients necessary for obtaining them can be found, for example in: "Tecnología farmacéutica", by J. L. Vila Jato, 1997 Vols I and II, Ed. Sintesis, Madrid; or in "Handbook of pharmaceutical manufacturing formulations", by S. K. Niazi, 2004 Vols I to VI, CRC Press, Boca Raton.

The quantity of active ingredient (antibodies) that can be combined with the vehicle to make a single dose form will generally be the quantity that produces a therapeutic effect. The preparation of a parenteral pharmaceutical composition in the form of dosage units facilitates the administration and uniformity of the dose, so this is very beneficial. These dosage units can be prepared by a person skilled in the art according to conventional techniques and taking into account the specific therapeutic effect that is desired to be achieved and the specific therapeutic indication.

The effective dose of the pharmaceutical composition of the invention will depend on multiple factors, including the methods and ways of administration, target site of action, the patient's physiological state, other administered medications, of if this is a prophylactic or therapeutic treatment. However, in a particular embodiment, the dosage unit to be administered of the neutralising antibody of the invention will be between 1.0 and 10.0 mg/kg. Typically, the administration regime will include repeated administration of the composition with the antibodies of the invention, with intervals between each administration that can be daily, weekly, monthly, bimonthly or any other that the pharmacologist establishes according to the needs of the patient (specific indication, severity, etc.) and depending on the common standard pharmacological protocols.

EXAMPLES OF THE INVENTION

The examples illustrating the effects on fibrinolytic and thrombolytic activity of the matrix metalloproteinases MMP-10 and MMP-3, either directly or in combination with other plasminogen activators: urokinase (uPA) and tissue plasminogen activator (tPA) are described below.

For the examples, the following were used:
recombinant MMP-10, obtained as a pro-enzyme of 58 kDa with 20-30% of mature enzyme of 48 kDa (R&D Systems, 910-MP, Abingdon, UK), which was reconstituted with TCNB buffer (50 mM Tris-HCl, pH 7.5, 10 mM $CaCl_2$, 150 mM NaCl, 0.05% Brij35).

recombinant MMP-3, obtained as a pro-enzyme of 52 kDa (R&D Systems, 513-MP, Abingdon, UK), supplied in a solution with 12.5 mM Tris, 5 mM $CaCl_2$, 0.025% Brij35 and 50% glycerol.

Urokinase (uPA) (Vedim Pharma SA; 628602, Barcelona, Spain).

Recombinant tissue plasminogen activator (tPA) (Boerhinger Ingelheim; 985937 Actilyse®, Ingelheim, Germany).

For the evaluation of the thrombolytic activity, a turbidimetric method was used to monitor the formation and lysis of the fibrin clot on samples of plasma, in accordance with the protocol previously described by von dern Borne and collaborators [Blood, 1995; 86: 3035-3042].

Also, to evaluate the activity on fibrin lysis, assays on fibrin plaques following the procedure described by Edward [J. Clin. Path., 1972; 25: 335-337] were used.

Example 1

Effect of MMP-10 and MMP-3 on the Formation and Lysis of Clots

As previously mentioned, the effect of MMP-10 and MMP-3 on the haemostatic system was evaluated according to the procedure described by von dern Borne et al. In this method, the changes in turbidity/absorbance as an indicator during the formation and lysis of clots were evaluated over time for both processes. The measurement of turbidity was performed by reading the absorbance at 405 nm during the formation and lysis phases of clots, using a photometric reader, in our case an ELISA reader (Fluostar Optima, BMG Labtech). The increase in turbidity/absorbance indicates the formation of the fibrin clot while the decrease in this parameter indicates the lysis of the clot.

For the formation of the clot, 75 µl of citrated plasma, 75µ of HEPES buffer (25 mM HEPES, 137 mM NaCl, 3.5 mM KCl, 6 mM $CaCl_2$, 1.2 mM $MgCl_2$, and 0.1% BSA, pH=7.5) and 10 µl of 150 mM $CaCl_2$ were mixed in a microplate well. The plate was incubated at 37° C. and the absorbance of 405 nm measured for 2 h, with readings every 30 seconds.

To study the effect of MMP-10 on the formation of the clot, activated MMP-10 (50, 100 and 200 nM) was added to the initial mixture of plasma and HEPES buffer. Before its use in experiments, MMP-10 was activated by thermal treatment at 37° C. for 1 hour.

In parallel assays, the effect on the formation of clots with MMP-3 (200 nM) was also analysed. In this case, MMP-3 was first activated with 1 mM p-aminophenylmercuric acetate (APMA, 164610, MD Biosciences, La Jolla, USA) at 37° C. for 24 h.

As can be seen in FIG. 1A, MMP-10 did not induce changes in the speed of clot formation nor on the maximum turbidity reached, at any of the doses used (Table 1). However, MMP-3 induced a decrease of 50% in the maximum absorbance/turbidity of the clot formed, probably by its direct proteolytic action on fibrinogen.

These results show that MMP-10, in contrast to that described for MMP-3, does not alter the rate of formation of the clot as it does not have any activity against fibrinogen.

Then, the rate of fibrin clot lysis was studied. As in the previous section, recalcified plasma in HEPES buffer was used, to which MMP-10 (or MMP-3) was added simultaneously with a plasminogen activator, chosen from 30 U/ml tissue plasminogen activator (tPA) or 135 U/ml urokinase (uPA) at the start of turbidimetric measurements.

The concentrations of tPA and uPA to be used were determined in previous dose-response studies where the selected dose was that which completely lysed the fibrin clot in the space of 2 h.

As can be seen in FIG. 1B and Table 1, MMP-10 in the absence of tPA and uPA did not cause lysis of the fibrin clot, while in the presence of the two activators, tPA or uPA, it induced a significant increase in the rate of lysis of the fibrin clot. With the maximum dose of MMP-10 tested (200 nM), the reduction in lysis time (time in which half the clot was lysed) was 15 min (52.9 min vs 68.3 min, $p<0.01$) in the presence of tPA and 5 min in the presence of uPA (42 min vs 47.5 min), $p<0.05$). This reduction in lysis time represents a 20% reduction in the presence of tPA and 10% with uPA.

By contrast, MMP-3 did not change the rate of clot lysis in the presence of tPA.

These results indicate that MMP-10, in contrast to MMP-3, is not able to digest fibrin, but increases the fibrinolytic effect of plasminogen and fibrinolysis (tPA and uPA) activators. MMP-10, not having the capacity to act on endogenous fibrinolysis, would prevent or attenuate the beginning of haemorrhaging, which makes it a good candidate for use as co-adjuvant in thrombolytic therapy.

TABLE 1

Lysis time of fibrin clot (expressed in minutes) in the presence of plasminogen activators (tPA or uPA)

|  | tPA 30 U/ml | tPA 20 U/ml | tPA 15 U/ml | uPA 135 U/ml |
|---|---|---|---|---|
| Control | 68.3 | 102.0 | 125.3 | 47.5 |
| MMP-10 50 nM | 65.5 | — | — | — |
| MMP-10 100 nM | 61.2 | — | — | — |
| MMP-10 200 nM | 52.9 | 84.7 | 108.7 | 42.0 |
| MMP-2 200 nM | 76.3 | — | — | — |
| Anti-MMP-10 (MAb) | No lysis | — | — | No lysis |
| IgG isotype control | 74.3 | — | — | 48.3 |

Example 2

Effect of MMP-10 on the Degradation of Fibrin

In accordance with the above-mentioned Edward's procedure, the effect on fibrin lysis was studied by measuring the halo or area of lysis that occurred on a polymerised fibrin plaque.

The fibrin plaques were prepared starting with a solution of 6 mg/ml of human fibrinogen (Sigma, F3879, Saint Louis, Mo., USA) in veronal buffer (BioWhittaker, 12-624E, Cambrex, Md., USA) at 37° C., which was filtered, and to which an equal volume of 50 mM $CaCl_2$ was added. This solution (6 ml) was mixed with 1 international unit (NIH units) of thrombin (Enzyme Research Lab; HT1200a, Swansea, UK) and was allowed to polymerise for 6 h.

To evaluate fibrinolytic capacity, on different fibrin plaques, tPA (1 U/ml), MMP-10 (200 nM), or a combination of both were added.

Figure 2:
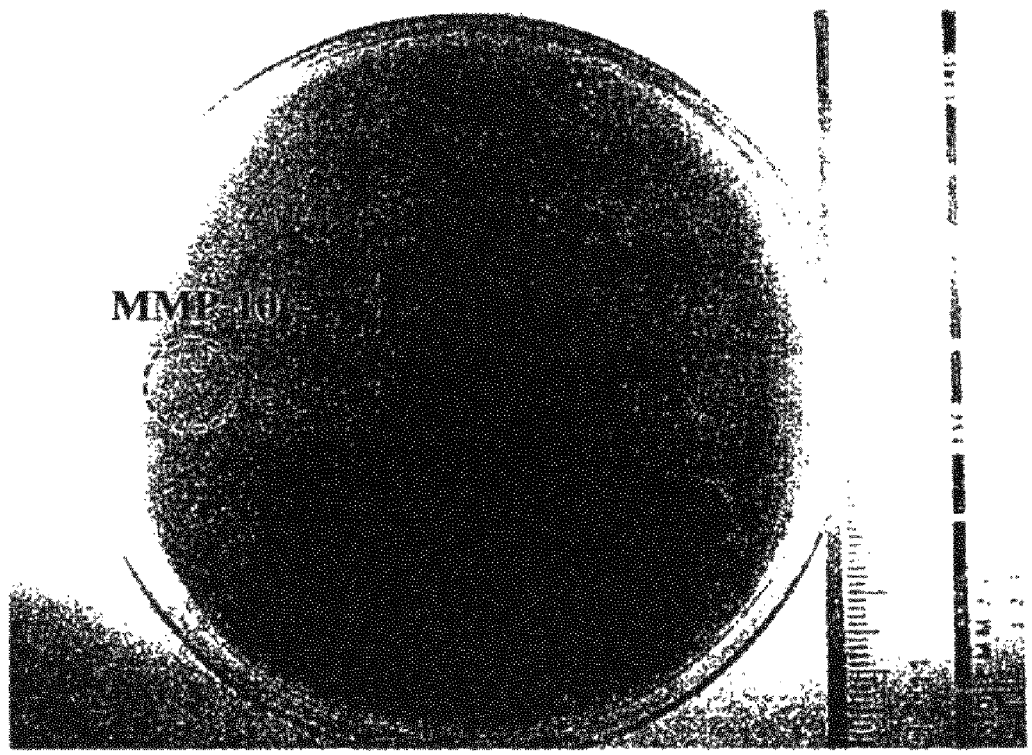
FIG. 2. Polymerised fibrin plaque in which areas of lysis produced by tPA (1 U/ml) and MMP-10 (200 nM) alone or added together are shown.

As can be seen in FIG. 2, MMP-10 alone did not produce lysis of the polymerised fibrin, while tPA produced a marked halo. However, the combination of tPA with MMP-10 significantly increased the area of lysis of polymerised fibrin (188.6%), a fact that confirms the facilitating effect of MPP-10 on fibrinolysis in combination with plasminogen activators as fibrinolytic agents.

Example 3

Inhibition of Fibrinolysis and Clot Lysis Induced by tPA with Anti-MMP-10 Antibodies In accordance with the results of Examples 1 and 2, the specificity of the effect of MMP-10 on fibrin lysis in the clot induced by tPA was analysed by simultaneously adding different doses of active MMP-10, in the presence (ratio 1:2) and absence of a monoclonal antibody that blocked its activity (R&D Systems, MAB9101, Abingdon, UK), or of a murine IgG2B isotype control (eBioscience, 16-4732, San Diego, Calif., USA) at the same concentration.

Figure 3:
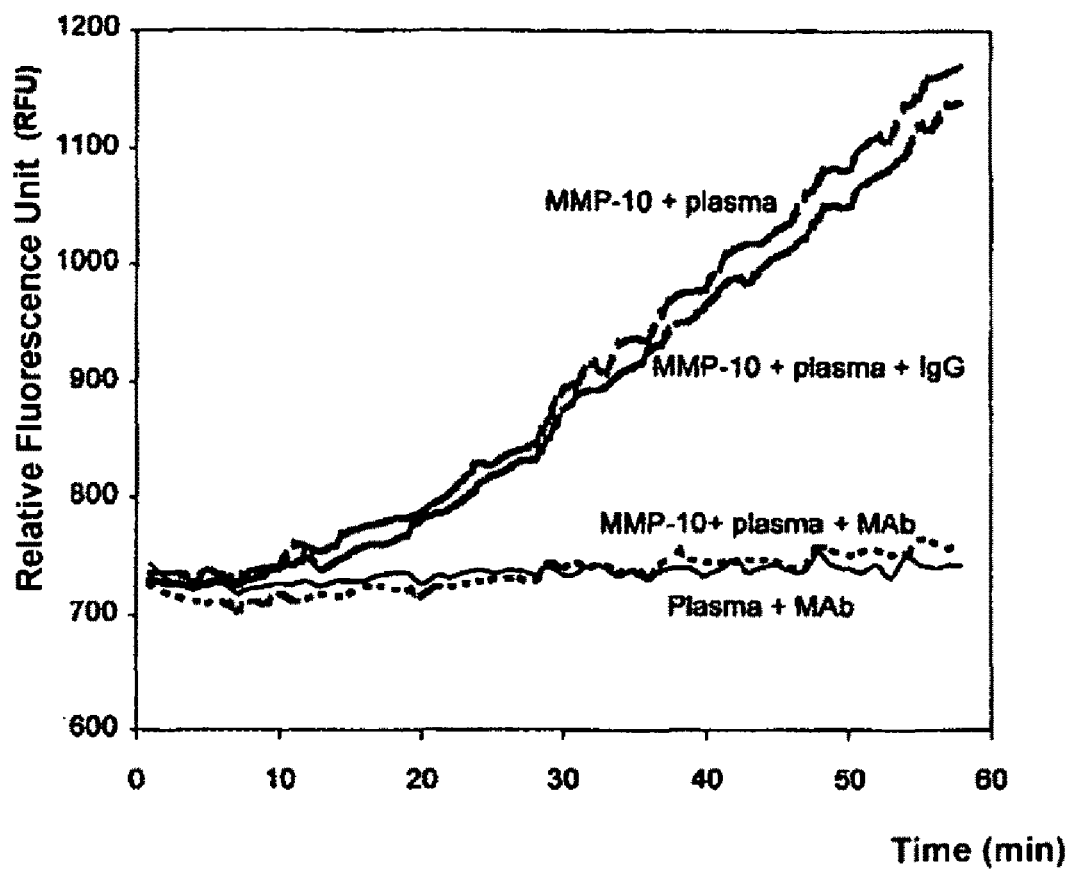
FIG. 3. Assay of MMP-10 (100 nM) activity in plasma with a fluorescent substrate of stromelysins. The concentration of the monoclonal antibody (MAb) that inhibits the activity of MMP-10 in plasma was determined by the reduction in the substrate formation gradient. An IgG isotype antibody was used as a control.

The ratio of enzyme:antibody that blocked the enzyme activity was previously tested in an activity trial for MMP-10 in a microplate coated with an anti-MMP-10 antibody (R&D systems, Clon110343) and using the fluorogenic stromelysin substrate (MCA-Arg-Pro-Lys-Pro-Val-Glu-Nval-Trp-Arg-Lys-[DNP]-NH2) (R&D systems; ES002, Abingdon, UK) [Lombard et al.; Biochimie, 2005; 87: 265-272]. The fluorescence (320 nm excitation and 405 nm emission) was measured in a spectrofluorometer (SpectraMAX GeminiXS, Molecular Devices, CA, USA) for 1 h, establishing that the ratio 1:2 completely inhibited the concentration of active enzyme (FIG. 3).

Figure 4:
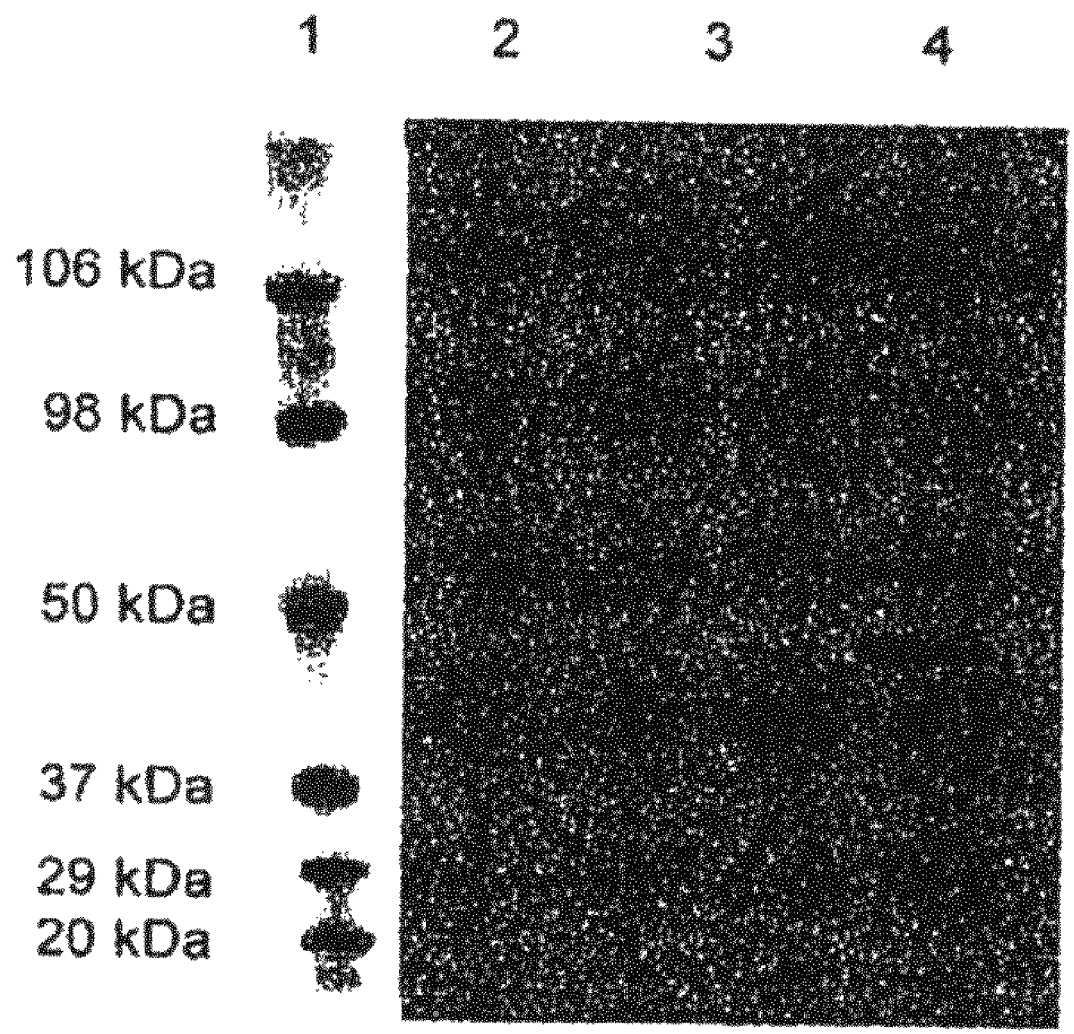
FIG. 4. Western blot with the antibody that inhibits the activity of MMP-10. Molecular weight marker (lane 1), MMP-1 (lane 3), MMP-3 (lane 3), MMP-10 (lane 4). The antibody inhibitor of MMP-10 activity only recognises the MMP-10 proenzyme (55 kDa) and the active enzyme (45 kDa), without showing any cross reaction with other metalloproteases.

The specificity of the antibody was studied by Western blot to discard the existence of cross reaction with other metalloproteases (FIG. 4). The MMP-10 inhibitor antibody only recognised this metalloprotease, so it exercised specific inhibition over it, despite the high homology in the metalloproteases family and in particular with the other stromelysin MMP-3.

Figure 5:
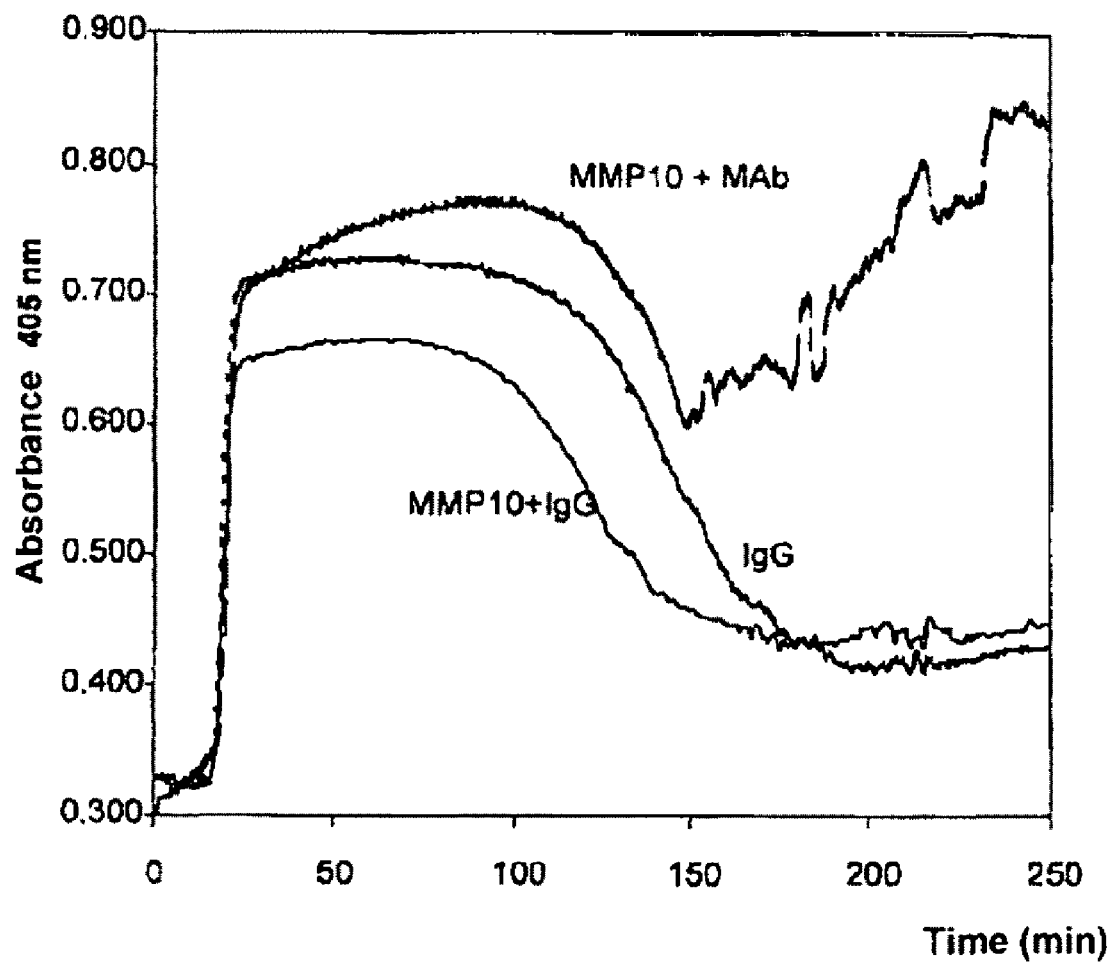
FIG. 5. Turbidimetric assay of plasma recalcified with MMP-10 (200 nM) in the presence or absence of a monoclonal antibody (MAb) that inhibits the activity of MMP-10, and of an IgG isotype control antibody.

The results show that the co-adjuvant effect on fibrinolysis is specific to MMP-10 as this is reduced in the presence of anti-MMP-10 antibody. This effect was very striking when said antibody was added to block the endogenous activity of plasma MMP-10 (FIG. 5). The results establish that the absence of MMP-10 in plasma prevents lysis of the fibrin clot even in the presence of tPA or uPA (Table 1).

Figure 6:
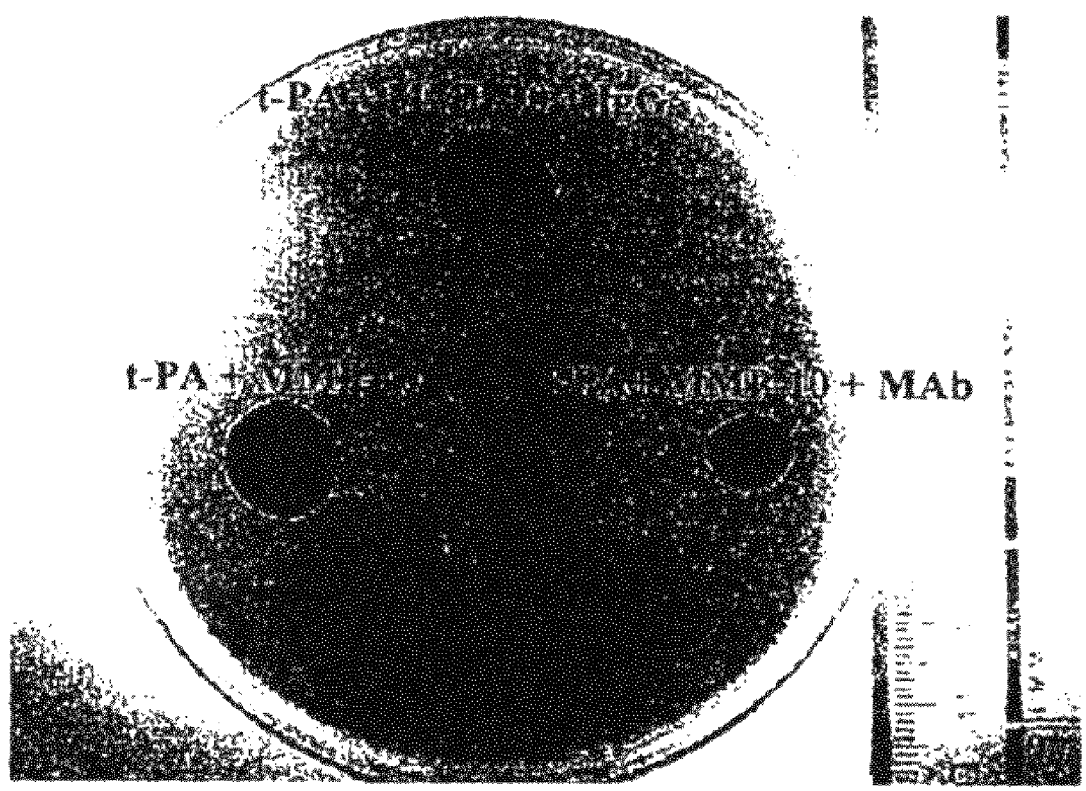
FIG. 6. Fibrin plaque showing the differences in the area of lysis produced by tPA (1 U/ml) and MMP-10 (200 nM) in the presence or absence of a monoclonal antibody that inhibits the activity of MMP-10 (MAb) and an IgG isotype control antibody.

These results were corroborated in trials on polymerised fibrin plaques. As shown in FIG. 6, in the presence of anti-MMP-10 antibody, the area of lysis produced by the combination tPA:MMP-10 was reduced (91.2% vs 188.6%), while the control antibody had no effect (184.6%). These data confirm that the use of a specific antibody for MMP-10 neutralises and blocks the pharmacological dissolution of fibrin clots.

Example 4

Haemorrhage Time

To analyse the effect of the absence of MMP-10, the haemorrhage time in 17 MMP-10 knockout mice (KO) and 14 wild mice (WT) of 1 month in age was studied. The animals were anaesthetised with a mixture of ketamine (100 mg/kg) and xylazine (5 mg/kg) intraperitoneally and were kept on a thermal blanket at 37° C. The last 5 mm of the tail was cut with a scalpel and submerged in 1 ml of 0.9% NaCl at 37° C. The time from the start of bleeding to when the blood stopped flowing spontaneously was measured. Also, the amount of blood loss was measured by the absorbance of the blood collected in the saline solution at 560 nm and the result was compared with a standard curve constructed with known volumes of mice blood.

Results

The haemorrhaging time provides an additional measure of haemostasis in vivo.

As can be seen in Table 2, the haemorrhaging time in MMP-10 KO mice was significantly less than that shown by wild mice. The blood loss during the time of haemorrhage was significantly lower, which indicates that in the absence of MMP-10, the capacity to control haemorrhage is greater than when it is present.

TABLE 2

|  | MMP-10 KO | (WT) | p |
|---|---|---|---|
| Haemorrhage time (s) | 44.0 ± 24.4 | 98.9 ± 64.0 | 0.008 |
| Blood loss (µl) | 4.2 ± 0.9 | 12.1 ± 12.1 | 0.036 |

The invention claimed is:

1. Method for anti-fibrinolytic treatment in a subject comprising administering to the subject an effective amount of a neutralising antibody for matrix metalloproteinase-10 (MMP-10).

2. The method according to claim 1 for treatment of haemorrhaging and haemorrhagic complications.

3. The method according to claim 2 for the treatment of haemorrhaging and haemorrhagic complications in patients with hyper-fibrinolytic states caused by congenital abnormalities.

4. The method according to claim 2 for the treatment of haemorrhages and haemorrhagic complications in patients receiving anticoagulant treatment.

5. The method according to claim 2 for the treatment of haemorrhages and haemorrhagic complications in patients with disseminated intravascular coagulation.

6. The method according to claim 2 for treatment of haemorrhages and haemorrhagic complications caused by surgical procedures.

7. The method according to claim 2 as an alternative to blood transfusion in acute haemorrhaging.

* * * * *